United States Patent
Willis et al.

[11] Patent Number: 5,813,991
[45] Date of Patent: Sep. 29, 1998

[54] ENDOCARDIAL MAPPING SYSTEM AND METHOD

[75] Inventors: N. Parker Willis, Atherton; Marsha Hurd, Clayton; Donald Chin, Palo Alto, all of Calif.

[73] Assignee: Cardiac Pathways Corporation, Sunnyvale, Calif.

[21] Appl. No.: 842,942

[22] Filed: Apr. 25, 1997

[51] Int. Cl.[6] .................................................. A61B 55/04
[52] U.S. Cl. ............................ 600/510; 600/522; 606/42
[58] Field of Search .................................... 600/374, 510, 600/522; 128/701; 607/122, 13; 606/35, 42

[56] References Cited

U.S. PATENT DOCUMENTS

| | | | |
|---|---|---|---|
| 4,579,119 | 4/1986 | Callaghan .................................. | 607/13 |
| 4,903,700 | 2/1990 | Whigham et al. ......................... | 607/13 |
| 5,357,956 | 10/1994 | Nardella .................................. | 600/374 |
| 5,433,198 | 7/1995 | Desai ....................................... | 607/122 |
| 5,553,611 | 9/1996 | Budd et al. ............................... | 600/374 |

OTHER PUBLICATIONS

Kahn, Hafiza H. et al., Activation Times in and Adjacent to Reentry Circuits . . . American Heart Journal, Apr. 1994, pp. 833–842.

Primary Examiner—William E. Kamm
Assistant Examiner—George R. Evanisko
Attorney, Agent, or Firm—Flehr Hobbach Test Albritton & Herbert LLP

[57] ABSTRACT

Endocardial system and method in which noise and artifacts introduced by a simulator are decoupled from a recorder by connecting the stimulator to the electrodes used for pacing and recording only when it is necessary to do so. At other times, the stimulator is disconnected, and low level signals are recorded without interference from the stimulator. In one embodiment, the stimulator is connected only during the time the pacing pulse is being delivered. In another, a stimulator which delivers pacing pulses in response to intrinsic activation of tissue at the pacing site is connected during delivery of a pacing pulse, disconnected during the measurement period which follows, and then reconnected so that it can sense further intrinsic activity and deliver another pacing pulse.

15 Claims, 3 Drawing Sheets

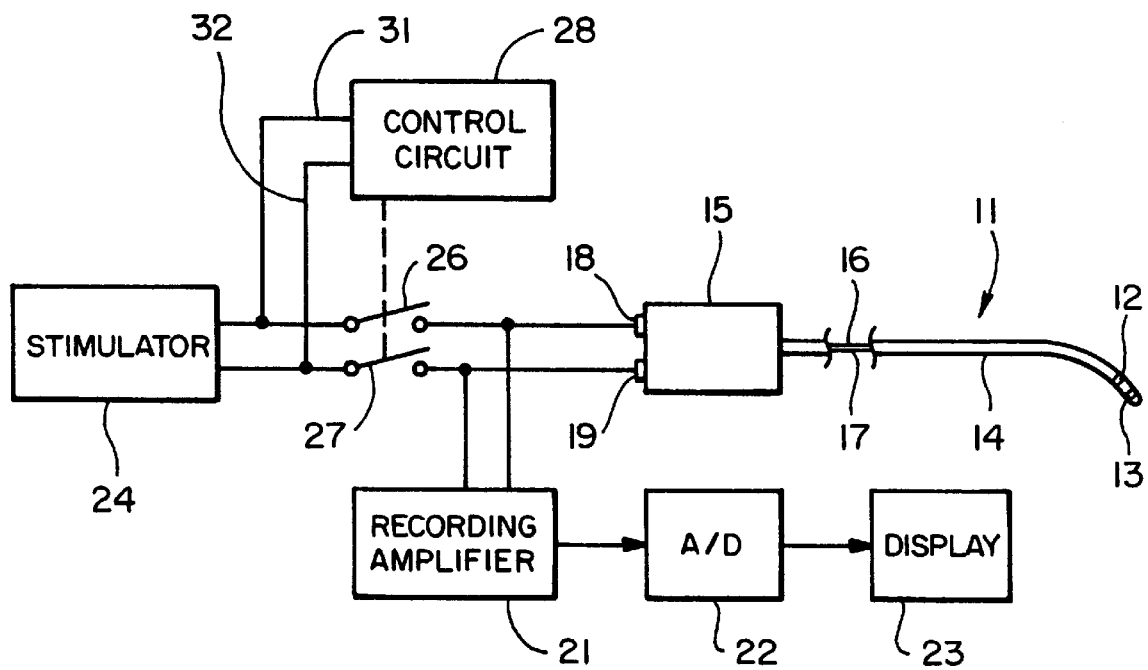
FIG_1
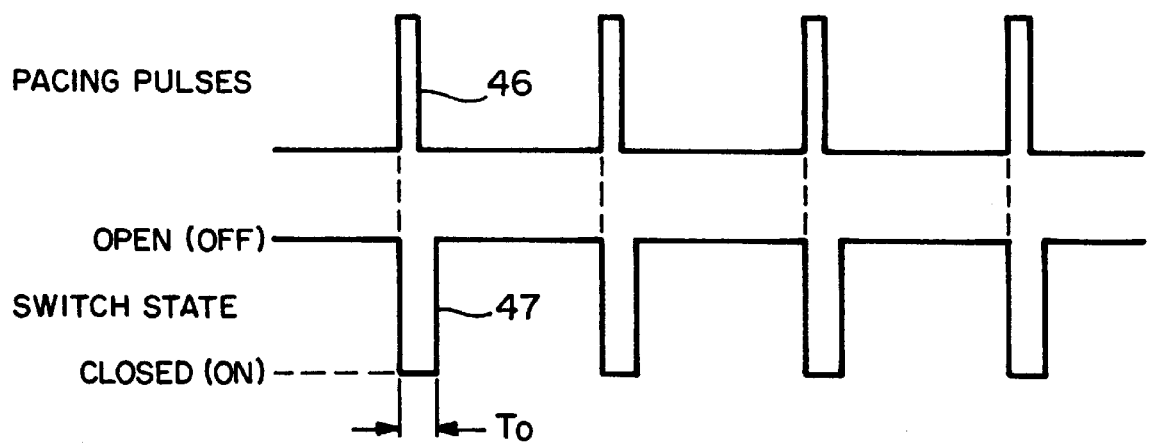
FIG_3

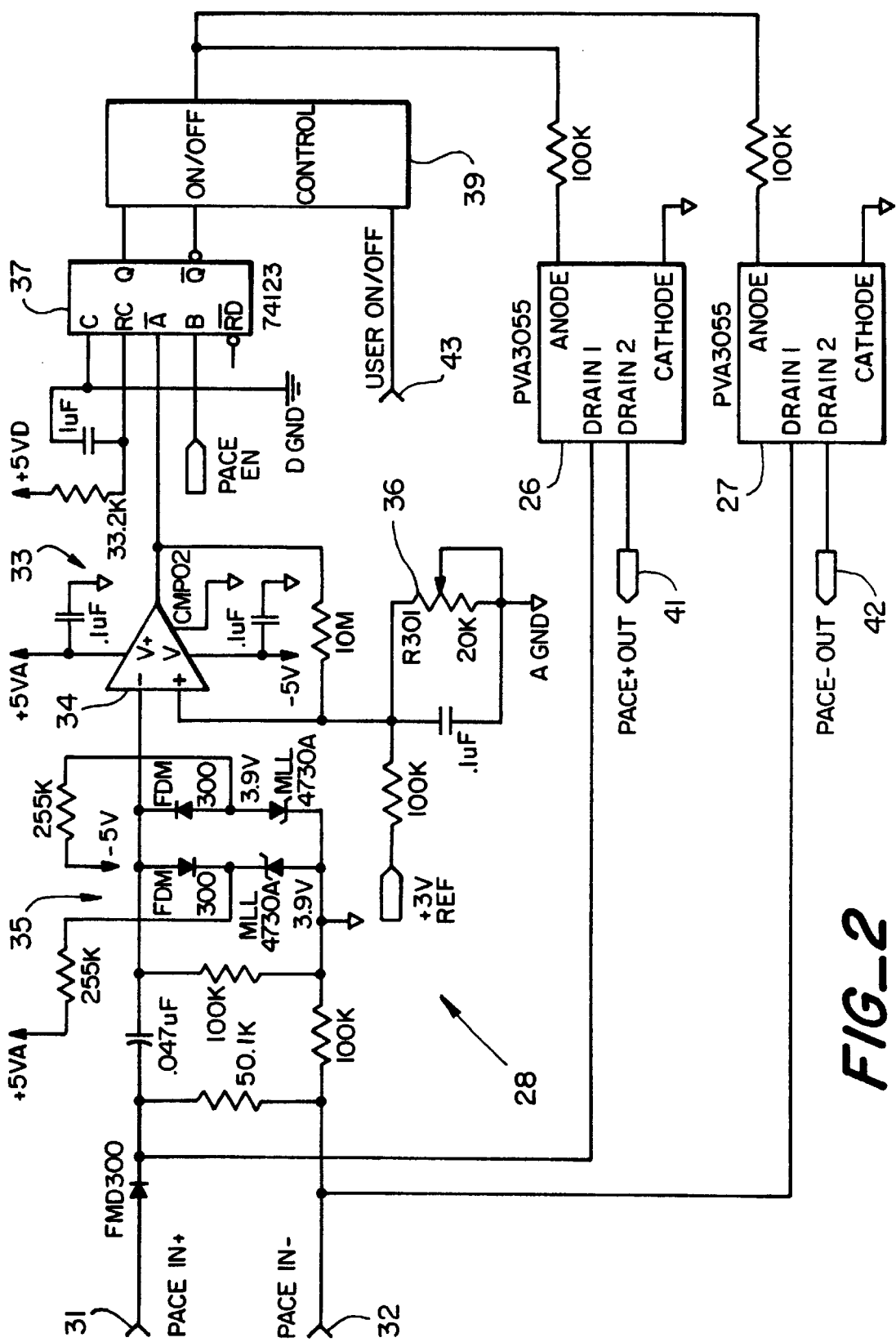
FIG_2

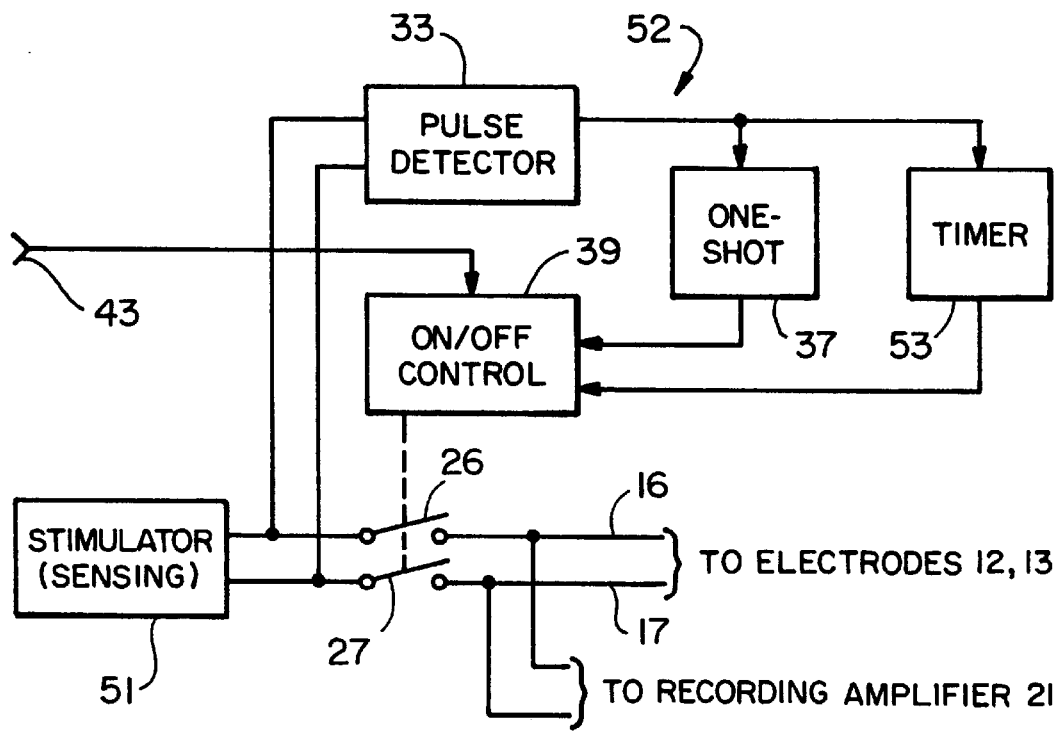
FIG_4
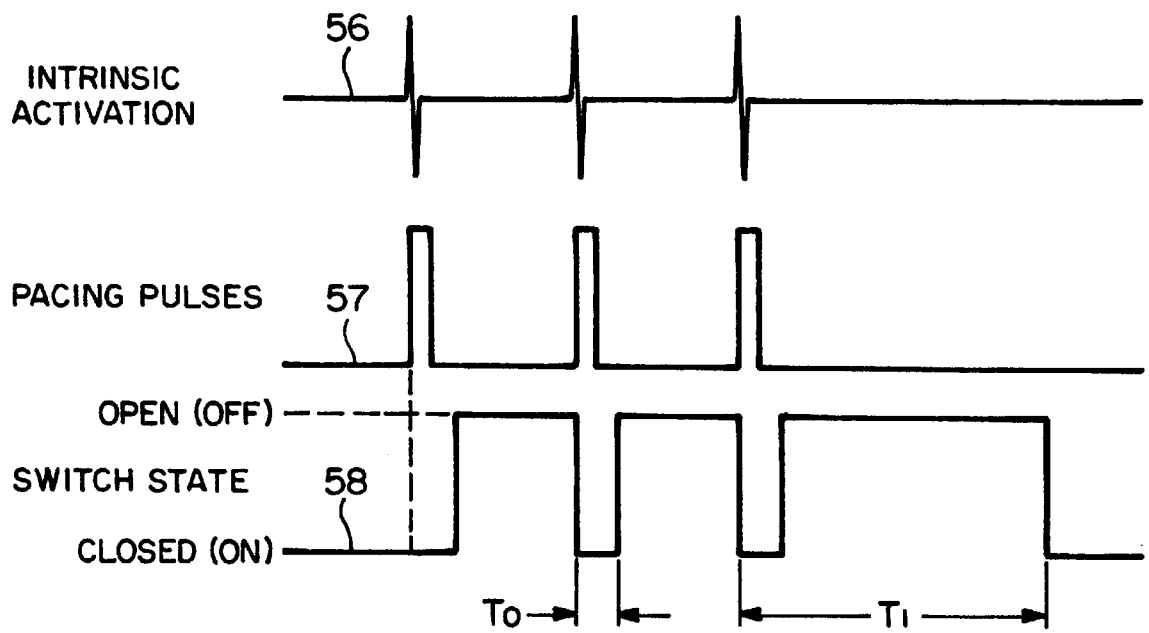
FIG_5

ENDOCARDIAL MAPPING SYSTEM AND METHOD

This invention pertains generally to endocardial mapping and, more particularly, to a system and method for reducing electrical noise and pacing artifacts when electrograms are recorded from a pacing site.

In some types of cardiac mapping, such as entrainment mapping, it is desirable to use the same electrodes both for stimulation and for recording from a given site. By simultaneously recording signals from multiple sites, it is possible to delineate substantial portions of an arrhythmiagenic circuit or loop in the heart.

Entrainment mapping has, for example, been employed to distinguish bystander areas of abnormal electrical activity from reentry circuit sites in myocardial infarct scars. Pacing at a reentry circuit site entrains the ventricular tachycardia which results from the scar, and analysis of electrograms at the pacing site is useful in identifying sites which are within the reentry circuit and sites which are not. However, recording of electrograms at a pacing site is subject to electrical noise and pacing artifacts, which can make assessment of the postpacing interval rather difficult. The noise comes from two principal sources: (1) the cabling required to connect a stimulator to the electrodes carried by a catheter, and (2) the internal wiring and circuitry of the stimulator. This makes the design of a low noise cardiac amplifier for use in a recording system very difficult because the designer of the system generally has no control over either the type of pacer or the length of the cabling that will be used with it.

The problem is complicated by the fact that stimulation voltages are generally on the order of tens of volts (e.g., 40 volts), whereas the voltages which must be recorded may be as small as 100 microvolts. Also, most bioamplifiers have a relatively low D.C. compliance voltage (e.g., 10–50 millivolts), and it takes a long time to get back to that level from the level of the stimulation voltage (e.g., 40 volts).

Artifacts on a pacer signal consist of a tail following each pacer pulse. The pacer pulses are square, and the polarity of the tail is opposite to that of the pulse, with the area under the tail being equal to the area under the pulse. The tail typically has a magnitude on the order of tens of millivolts, and it may persist for a period of time on the order of 40–100 milliseconds. Such voltages are outside the D.C. compliance levels of most bioamplifiers, and they reduce the amount of time the system has to recover from a pacer pulse and be ready for the next measurement. For arrhythmias of up to 300 heartbeats per minute, cardiac activity is typically measured at intervals of 200 milliseconds, and a tail of 40–100 milliseconds leaves only about 100–160 milliseconds for the system to prepare for the next measurement.

In order to avoid the problems associated with pacer noise and artifacts, some electrophysiologists have tried pacing at one site and recording at another. Such a study is described in a paper entitled "Activation Times in and Adjacent to Reentry Circuits During Entrainment: Implications for Mapping Ventricular Tachycardia", by Hafiza H. Khan, M.D., and William G. Stevenson, M.D., American. Heart Journal, Apr. 1994, pp. 833–42.

It is in general an object of the invention to provide a new and improved endocardial mapping system and method in which electrical noise and pacing artifacts are reduced.

Another object of the invention is to provide an endocardial system and method of the above character which enables pacing and recording to be done with the same electrodes.

These and other objects are achieved in accordance with the invention by providing an endocardial system and method in which noise and artifacts introduced by a stimulator are decoupled from a recorder by connecting the stimulator to the electrodes only when it is necessary to do so. At other times, the stimulator is disconnected, and low level signals are recorded without interference from the stimulator. In one disclosed embodiment, the stimulator is connected only during the time the pacing pulse is being delivered. In another, a stimulator which delivers pacing pulses in response to intrinsic activation of tissue at the pacing site is connected during delivery of a pacing pulse, disconnected during the measurement period which follows, and then reconnected so that it can sense further intrinsic activity and deliver another pacing pulse.

FIG. 1 is a block diagram of one embodiment of an endocardial mapping system incorporating the invention.

FIG. 2 is a circuit diagram of the controller and switches in the embodiment of FIG. 1.

FIG. 3 is a waveform diagram illustrating operation of the embodiment of FIG. 1.

FIG. 4 is a partial block diagram of another embodiment of an endocardial mapping system incorporating the invention.

FIG. 5 is a waveform diagram illustrating operation of the embodiment of FIG. 4.

As illustrated in FIG. 1, the system includes a catheter 11 which has a pair of electrodes 12, 13 located toward its distal end. The catheter has an elongated flexible tubular body 14 which is attached at its proximal end to a handle or controller 15. Electrical leads 16, 17 are connected to the electrodes and extend through a lumen in the tubular body to connectors 18, 19 on the handle.

For ease of illustration, only one pair of electrodes and one pair of leads are shown in the drawings. However, it will be understood that the catheter can be provided with additional electrodes and leads for pacing and recording at different sites within the heart.

A recording amplifier 21 is connected to leads 16, 17 via connectors 18, 19 for monitoring electrical activity, or electrograms, at the site within the heart where electrodes 12, 13 are positioned. This amplifier can be a type commonly employed in mapping systems but with a higher D.C. compliance voltage. The output of the amplifier is connected to the input of an analog-to-digital (A/D) converter 22, and the output of the A/D converter is connected to a display 23 which provides a visual display of the recorded signals.

In one presently preferred embodiment, amplifier 21 has a D.C. compliance voltage on the order of 2 volts, and the A/D converter is a 14-bit converter. In contrast, in prior systems where pacing and recording have been attempted at the same time, the A/D converters have been only 12 bits wide, and the recording amplifiers have required a much lower D.C. compliance voltage (e.g., 50 millivolts). In the mapping system of the invention, the A/D converter preferably has a resolution greater than 12 bits, and the compliance voltage is on the order of 1 to 10 volts. The higher compliance voltage is a significant advantage in entrainment mapping.

A stimulator or pacer 24 of conventional design supplies pacing signals in the form of pulses which typically have a width on the order of 10 milliseconds or less and a magnitude on the order of 40 volts or less.

The stimulator is connected to the electrodes by means of switches 26, 27 which are closed (conducting) while the pulses are being delivered and open (nonconducting) at other times. Operation of the switches is controlled by a control circuit 28 which is illustrated in greater detail in FIG. 2.

The control circuit has input terminals 31, 32 to which the pacing signals are applied. The input terminals are connected to a pulse detector 33 which detects the leading or rising edges of the pacer pulses. The pulse detector includes a comparator 34 to which the pulses and a reference signal are applied. Overvoltage protection for the comparator is provided by a diode network 35, and the level of the reference signal is set by a potentiometer 36.

The output of the pulse detector is connected to the trigger input of a one-shot multivibrator 37 which delivers an output signal having a period ($T_0$) slightly greater than the widest expected pacing pulse, e.g. about 13 milliseconds.

The output of the one-shot is connected to an ON/OFF control 39 which controls the operation of switches 26, 27 which, in the embodiment illustrated, are solid state switching devices. The pacing pulses from input terminals 31, 32 are applied to the inputs (drain 1) of the switching devices, and the outputs (drain 2) of those devices are connected to output terminals 41, 42 to which the electrode leads are connected.

The ON/OFF control also includes a manual override input 43 which enables the user to manually close the switches in the event that it is desired to have the stimulator connected continuously to the electrodes.

Operation and use of the embodiment of FIG. 1, and therein the method of the invention, are as follows. The catheter is inserted into the body through the cardiovascular system, with electrodes 13, 14 positioned at a site within the heart where activity is to be monitored. Recording amplifier 21 is connected to the electrodes continuously for recording electrical activity, or electrograms, at the site. When stimulator 24 delivers a pacing pulse, switches 26, 27 close and apply the pulse to the electrodes. Upon termination of the pulse, or shortly (i.e., a few milliseconds) thereafter, the switches open, disconnecting the stimulator from the electrodes. The switches remain open until the next pulse is delivered by the stimulator. This operation is illustrated in FIG. 3, wherein the pacing pulses are represented by waveform 46 and the operation of the switches is represented by waveform 47.

The recorder is subjected to noise from the stimulator only during the brief interval that the switches are closed and the pacing pulses are being delivered. At all other times, the stimulator is decoupled from the recorder, and low noise recordings can be made.

Alternatively, rather than using a one-shot and turning the switching circuit off at a predetermined time after the leading edge of the pacer pulse, the trailing or falling edge of the pulse can be utilized for that purpose. In that case, an edge detector of conventional design detects the trailing edge of the pacer pulse, and the output of the edge detector turns off the switching circuit.

In the embodiment shown in FIG. 4, the stimulator 51 has a built-in sensor which detects the occurrence of inherent activation of tissue at the pacing/recording site and delivers a pacing pulse in response thereto. That synchronizes the pacing pulses with the intrinsic activation of the tissue being paced. Stimulator 51 is connected to catheter electrodes 12, 13 by switches 26, 27 which are controlled by a control circuit 52.

Control circuit 52 is similar to control circuit 28, with the addition of a timer 53 between the output of pulse detector 33 and ON/OFF control 39. Timer 53 comprises a one shot multivibrator having a period ($T_1$) corresponding to the longest interval over which noise-free recordings are desired (e.g., 2 seconds). It causes the ON/OFF control to reclose switching devices 26, 27 at the end of its period in the event that another pulse has not been delivered in the interim.

Operation and use of the embodiment of FIG. 4 are similar to that described above except for the second one-shot and the use of the sensing stimulator. That stimulator monitors signals from the electrodes and delivers a pacing pulse a predetermined time after inherent activation is detected. As in the embodiment of FIG. 1, the switches remain closed (conducting) for the duration of the pacing pulse, then open to disconnect the stimulator from the electrodes. The switches remain open until the rising edge of the next pacing pulse or until timer 53 times out, whichever occurs first. When the timer times out, the switches close and remain closed until further activation of the tissue at the pacing site is sensed.

This operation is illustrated in FIG. 5, wherein intrinsic activation is represented by waveform 56, the pacing pulses are represented by waveform 57, and the operation of the switches is represented by waveform 58.

The embodiment of FIG. 4 is not as effective at reducing noise as the embodiment of FIG. 1 because the system is left in a noisy state after a pacing run is completed. However, it does accommodate the sensing feature which is incorporated in to many pacers. It also permits low noise measurement of the post-pacing interval, which is a critical factor in entrainment mapping.

While only certain presently preferred embodiments have been described in detail, as will be apparent to those familiar with the art, certain changes and modifications can be made without departing from the scope of the invention as defined by the following claims.

Claims:

1. In an endocardial mapping system: a catheter having an electrode which can be positioned at a site within a heart, means connected continuously to the electrode for monitoring electrograms from the site, a stimulator for providing a pacing pulse, and means for connecting the stimulator to the electrode while the pacing pulse is being provided and disconnecting the stimulator from the electrode at times other when the pulse is being provided.

2. In an endocardial mapping system: a catheter having an electrode which can be positioned at a site within a heart, means connected to the electrode for monitoring electrograms from the site, a stimulator for providing a pacing pulse, and means responsive to a leading edge of the pacing pulse for connecting the stimulator to the electrode for a predetermined period of time after the occurrence of the leading edge.

3. The mapping system of claim 1 further including override means for connecting the stimulator continuously to the electrode.

4. In an endocardial mapping system: a catheter having an electrode which can be positioned at a site within a heart, means connected to the electrode for monitoring electrograms from the site. a stimulator which includes means for sensing intrinsic activation of tissue at the site and delivering a pacing pulse in response thereto, means for connecting the stimulator to the electrode for a predetermined period of time after the occurrence of a leading edge of the pacing pulse and thereafter disconnecting the stimulator from the electrode. and means for reconnecting the stimulator to the electrode a predetermined time after it is disconnected to permit further sensing at the site.

5. In a method of mapping electrical activity within a heart, the steps of: inserting a catheter into a body so that an electrode carried by the catheter is positioned at a site within the heart, monitoring electrograms from the site with a monitor which is continuously connected to the electrode, generating a pacing pulse with a stimulator, connecting the stimulator to the electrode while the pacing pulse is being generated, and disconnecting the stimulator from the electrode at times other than when the pacing pulse is being generated.

6. The method of claim 5 further including the step of overriding the step of disconnecting the stimulator, and keeping the stimulator connected continuously to the electrode.

7. In a method of mapping electrical activity within a heart, the steps of: inserting a catheter into a body so that an electrode carried by the catheter is positioned at a site within the heart, monitoring electrograms from the site with a monitor which is continuously connected to the electrode, generating a pacing pulse with a stimulator, and connecting the stimulator to the electrode for a predetermined period of time in response to a leading edge of the pacing pulse.

8. In a method of mapping electrical activity within a heart, steps of: inserting a catheter into a body so that an electrode carried by the catheter is positioned at a site within the heart, monitoring electrograms from the site with a monitor which is continuously connected to the electrode, sensing intrinsic activation of tissue at the site, delivering a pacing pulse, in response to such intrinsic activation, connecting the stimulator to the electrode for a predetermined period of time in response to a leading edge of the pacing pulse, thereafter disconnecting the simulator from the electrode, and reconnecting the stimulator to the electrode a predetermined time after it is disconnected to permit further sensing at the site.

9. In a method of mapping electrical activity within a heart, the steps of: inserting a catheter into a body so that an electrode carried by the catheter is positioned at a site within the heart, monitoring electrograms from the site with a monitor which is continuously connected to the electrode, generating a pacing pulse with a stimulator, connecting the stimulator to the electrode in response to a leading edge of the pacing pulse, and disconnecting the stimulator from the electrode in response to a trailing edge of the pacing pulse.

10. In a system for reducing recording noise in an endocardial mapping system in which a stimulator and a recorder are connected to the same electrodes on a catheter, the stimulator having means for sensing intrinsic activation of tissue at a site where the electrodes are positioned and delivering pacing pulses in response to such activation: switching means for alternatively connecting the stimulator to the electrodes and disconnecting the stimulator from the electrodes, and means responsive to the pacing pulses for controlling operation of the switching means such that the stimulator is connected to the electrodes for a predetermined period of time during the occurrence of a pacing pulse and thereafter is disconnected until another pacing pulse is detected, the means for controlling operation of the switching means including means for conditioning the switching means to reconnect the stimulator to the electrodes a predetermined time after it is disconnected.

11. In a system for reducing recording noise in an endocardial mapping system in which a stimulator that delivers pacing pulses and a recorder are conncted to the same electrodes on a catheter switching means for alternatively connecting the stimulator to the electrodes and disconnecting the stimulator from the electrodes, means responsive to pacing pulses from the stimulator for controlling operation of the switching means such that the stimulator is connected to the electrodes for a predetermined period of time during the occurrence of a pacing pulse and thereafter is disconnected until another pacing pulse in detected, and override means for connecting the stimulator continuously to the electrode.

12. In a method of reducing recording noise in an endocardial mapping system in which a stimulator that delivers pacing pulses and a recorder are connected to the same electrodes on a catheter, the steps of: connecting the stimulator to the electrodes while pacing pulses are being delivered by the stimulator, and disconnecting the stimulator from the electrodes during intervals between the pacing pulses, with the recorder being connected to the electrodes both while the pacing pulses are being delivered and while the stimulator is disconnected.

13. The method of claim 12 further including the steps of overriding the steps of disconnecting the simulator, and keeping the stimulator connected continuously to the electrode.

14. In a method of reducing recording noise in an endocardial mapping system in which a stimulator and a recorder are connected to the same electrodes on a catheter, the steps of: delivering pacing pulses from the stimulator in response to intrinsic activation of tissue at a site where the electrodes are positioned, connecting the stimulator to the electrodes while pacina pulses are being delivered by the stimulator. disconnecting the stimulator from the electrodes until another pacing pulse is delivered, and reconnecting the stimulator to the electrodes a predetermined time after it is disconnected in the event that another pacing pulse is not delivered within that time so that the stimulator can respond to further intrinsic activation at the site.

15. In an endocardial mapping system: a catheter having first and second electrodes adapted to be positioned at a site within a heart, means having first and second inputs connected continuously to respective ones of the electrodes for monitoring electrograms from the site, a stimulator having first and second outputs for providing pacing pulses, and means for connecting outputs of the stimulator to the electrodes while the pacing pulses are being provided and disconnecting the stimulator from the electrodes at times other when the pulses are being provided.

* * * * *